US008447537B2

(12) United States Patent
Bismarck et al.

(10) Patent No.: US 8,447,537 B2
(45) Date of Patent: May 21, 2013

(54) METHODS AND APPARATUS FOR DETERMINING THE PERMEABILITY AND DIFFUSIVITY OF A POROUS SOLID

(75) Inventors: Alexander Bismarck, Peterborough (GB); Geoffrey F. Hewitt, London (GB); Karen Shu San Manley, Reading (GB); Johnny W. Johnson, Duncan, OK (US)

(73) Assignees: Halliburton Energy Services, Inc., Duncan, OK (US); Imperial College London, London (GB)

( * ) Notice: Subject to any disclaimer, the term of this patent is extended or adjusted under 35 U.S.C. 154(b) by 281 days.

(21) Appl. No.: 12/711,697

(22) Filed: Feb. 24, 2010

(65) Prior Publication Data

US 2010/0268488 A1 Oct. 21, 2010

(30) Foreign Application Priority Data

Feb. 24, 2009 (GB) .................................. 0903110.5

(51) Int. Cl.
 *G01F 17/00* (2006.01)
 *G01N 15/08* (2006.01)

(52) U.S. Cl.
 USPC ................................................ 702/50; 73/38

(58) Field of Classification Search ............. 702/50, 702/23–24, 31, 45, 81, 84, 127, 137–138, 702/140, 182–183, 189; 73/1.02, 1.06, 1.16, 73/1.35, 1.57–1.58, 23.2, 23.24, 23.26–23.27, 73/23.29, 38, 64.46–64.47, 64.51, 861, 861.08, 73/861.42
See application file for complete search history.

(56) References Cited

U.S. PATENT DOCUMENTS

| 4,815,316 A | * | 3/1989 | Tantram | 73/38 |
| 5,265,462 A | * | 11/1993 | Blauch et al. | 73/38 |

FOREIGN PATENT DOCUMENTS

| GB | 2197080 A | 5/1988 |
| WO | 9966306 A1 | 12/1999 |
| WO | 2009024754 A1 | 2/2009 |

OTHER PUBLICATIONS

Feng et al., Multicomponent Diffusion of Gases in Porous Solids. Models and Experiments, 1974, Ind. Eng. Chem., Fundam., vol. 13, No. 1, pp. 5-9.*
Hewitt et al., The Diffusion of Oxygen in Nitrogen in the Pores of Graphite: The Effect of Oxidation on Diffusivity and Permeability, 1970, Carbon, vol. 8, Issue 3, pp. 271-282.*
Foreign communication from a related counterpart application—Search Report, United Kingdom application GB1003132.6, Apr. 27, 2010, 3 pages.
Ishizaki, Kozo, et al., "Porous materials: process technology and applications," Oct. 1998, 1 page, Kluwer Academic Publishers.
Foreign communication from a related counterpart application—Examination Report, United Kingdom application GB1003132.6, Jan. 16, 2013, 6 pages.

* cited by examiner

*Primary Examiner* — Toan Le
(74) *Attorney, Agent, or Firm* — Robert Kent; Conley Rose, P.C.

(57) ABSTRACT

An apparatus for measuring the permeability and diffusivity of a porous solid includes a device for measuring permeability of the solid; a device for measuring diffusivity of the solid; a sample chamber for holding a sample of the solid, the arrangement being such that the permeability and diffusivity can be measured without removing the sample from the sample chamber.

29 Claims, 2 Drawing Sheets

METHODS AND APPARATUS FOR DETERMINING THE PERMEABILITY AND DIFFUSIVITY OF A POROUS SOLID

CROSS-REFERENCE TO RELATED APPLICATIONS

This application is a filing under 35 U.S.C. 119 which claims priority to United Kingdom Patent Application No. GB 0903110.5, filed Feb. 24, 2009 and entitled "Methods and Apparatus for Determining the Permeability and Diffusivity of a Porous Solid," which is hereby incorporated herein by reference in its entirety for all purposes.

BACKGROUND TO THE INVENTION

The invention generally relates to apparatus and methods for determining both the permeability and the diffusivity of a porous solid.

Permeability is one of the most commonly measured properties of porous materials. It is the ease at which a fluid is able to flow through the material when a pressure gradient is applied or essentially the fluid conductivity of a porous material. Ishizaki et al. (1998) *Porous materials; process technology and applications* shows that measurements of permeability can provide information about the pore structure and the tortuosity of interconnected pores within a sample.

The prior art discloses a variety of methods and apparatus by which permeability of a porous solid sample is measured. These include the use of wetting liquids for the determination of permeability, permeability from mercury porosimetry, laser-polarised gas nuclear magnetic resonance for permeability measurements and image analysis for permeability prediction.

The diffusivity of a porous material is also a useful property to measure as it provides information on tortuosity as well as pore length. The prior art also discloses methods and apparatus for measuring this property.

It is an object of the invention to provide an improved way of measuring the permeability and diffusivity of a porous solid.

SUMMARY OF THE INVENTION

The present invention provides a method and apparatus for measuring both the permeability and diffusivity of a porous solid without the need to remove the solid sample from the apparatus. The apparatus can be easily reconfigured with a few minor adjustments to switch between the permeability set up and the diffusivity set up.

The present invention relates to apparatus and methods for measuring both the permeability and the diffusivity of a porous solid sample, whereby both sets of experimental techniques are performed on the solid sample without the sample being removed from the apparatus. The measurements of these values enable determination of permeability, tortuosity, effective porosity and effective pore length of porous solids with a wide range of permeabilities using a single piece of apparatus.

In preferred embodiments of the invention, including the ones described below, the first gas is nitrogen and the second gas is oxygen. The third gas is also nitrogen. In an alternative embodiment, the first and third gas may be oxygen and the second gas may be nitrogen. However, any gases that have relatively close molecular weight can also be used with the apparatus. In an alternative embodiment, helium and argon may be used. In this case, the first and third gases may be helium and the second gas may be argon, or, the first and third gases may be argon and the second gas may be helium.

According to certain embodiments of the invention, the apparatus used for taking both permeability and diffusivity measurements employs a pressure rise technique to measure gas permeability using a first gas. The gas pressure at one side of the porous medium is kept low and a constant higher pressure is maintained at the other side of the material. The first gas is collected as it passes through the pores of the porous solid material from the high pressure side to the low pressure side of the apparatus. The rate of pressure rise is measured and used to determine the viscous permeability and the effects of Knudsen diffusion at low and applied pressures.

The apparatus can then be simply adapted to measure diffusivity of the porous solid sample without removing the sample from the apparatus. The porous solid sample is initially saturated with a third gas, and a flow of a second gas is applied to a face of the sample. The second gas then flows from one side of the sample to the other where the increase in concentration of the second gas is measured until an equilibrium concentration is reached. These measurements are used to calculate the tortuosity, effective porosity and effective pore length of the porous solid sample.

In this embodiment, and in all the embodiments discussed below, the first and third gases may be the same type of gas (e.g. oxygen, nitrogen, argon or helium). In a more preferred embodiment, the first and third gases are the same gas and are provided from the same source.

According to one aspect of the invention, there is provided an apparatus for measuring the permeability and diffusivity of a porous solid comprising: a permeability measuring means for measuring permeability of the solid; a diffusivity measuring means for measuring diffusivity of the solid; a sample chamber for holding a sample of the solid, the arrangement being such that the permeability and diffusivity can be measured without removing the sample from the sample chamber.

In an embodiment, the permeability measuring means comprises a means for using a pressure rise technique. In an embodiment of the invention, the sample chamber comprises: an inlet side having an inlet; an outlet side having an outlet; a first flow line in fluid communication with the inlet side of the sample chamber; a second flow line in fluid communication with the outlet side of the sample chamber. In an embodiment of the invention, the apparatus further comprises a first valve disposed in the first flow line.

In an embodiment of the invention, the apparatus further comprises an evacuation means for evacuating the sample chamber, comprising: a third flow line in fluid communication with the inlet of the sample chamber and a vacuum pump; a fourth flow line in fluid communication with the outlet of the sample chamber and the vacuum pump; whereby the vacuum pump can selectively evacuate the inlet and/or the outlet side of the sample chamber. In an embodiment of the invention, the apparatus further comprises: a second valve disposed in the third flow line and a third valve disposed in the fourth flow line.

In an embodiment of the invention, the apparatus further comprises: a source of a first gas, which can be placed selectively in fluid communication with the first flow line, whereby the first gas can be delivered to the sample chamber via the first flow line; a first pressure measuring device for measuring pressure in the first flow line between the source of the first gas and the inlet side; a first gas collecting vessel which can be selectively placed in fluid communication with the second flow line, whereby the first gas can be collected from the outlet side of the sample chamber after it has permeated through the solid sample core; a second pressure measuring device for measuring pressure in the second flow line between the first gas collecting vessel and the outlet side of the sample chamber; and a timer for measuring the rate at which pressure on the outlet side of the sample chamber rises, whereby the apparatus can be used to measure the permeability of the porous solid sample. In an embodiment of the invention, the apparatus further comprises: a fifth flow line in fluid communication with the inlet side of the sample chamber with a fourth valve disposed in it; a sixth flow line in fluid communication with the outlet side of the sample chamber with a fifth valve disposed in it.

In an embodiment of the invention, the apparatus further comprises: a flow meter which can be selectively placed in fluid communication with the second flow line instead of the first gas collecting vessel, whereby the second flow line serves as a second gas outlet line; a source of a third gas in fluid communication with the fifth flow line, whereby the third gas can be delivered to the sample chamber via the fifth flow line to saturate the sample with the third gas; a third pressure measuring device for measuring pressure in the fifth flow line between the source of the third gas and the inlet side; a source of the second gas in fluid communication with the sixth flow line, whereby the second gas can be delivered to the sample chamber via the sixth flow line; a fourth pressure measuring device for measuring pressure in the sixth flow line between the source of the second gas and the outlet side; a second gas concentration indicator which can be selectively placed in fluid communication with the first flow line instead of the source of the first gas, whereby the first flow line serves as an outlet line for both the second and third gases, whereby the apparatus can be used to measure the diffusivity of the porous solid sample. In some embodiments, the source of the first gas and the source of the third gas comprise a single gas source of the same gas. In some embodiments, the apparatus further comprises a seventh flow line in fluid communication with the first flow line and an exhaust, whereby gas may flow through the seventh flow line to the exhaust, to relieve a build up of pressure in the sample chamber. In preferred embodiments, a sixth valve is disposed in the seventh flow line.

In certain embodiments, the sample chamber comprises: a plurality of discs secured together to define the sample chamber therein, wherein O-ring seals are situated between adjacent discs. In preferred embodiments the discs have an interengaging formation therein, the interengaging formation being arranged so that each disc can only properly interengage a specific one or the other discs.

According to another aspect of the invention, there is provided a method of measuring the permeability and the diffusivity of a porous solid sample comprising: measuring the permeability of the sample and subsequently measuring the diffusivity of the sample, or vice versa; wherein the solid sample is contained in a sample chamber, the arrangement being such that the permeability and diffusivity can be measured without removing the sample from the sample chamber. In preferred embodiments, the solid sample is sealed in a sample holder within the sample chamber prior to commencing the measurements of permeability and diffusivity. In preferred embodiments the sample chamber is first evacuated by vacuum pump prior to commencing measurement of the permeability and diffusivity.

In an embodiment, the method of measuring permeability comprises a pressure rise technique. In an embodiment of the invention, the method further comprises measuring the permeability of the solid sample by: selectively placing a source of a first gas in fluid communication with an inlet of the sample chamber; and selectively placing a first gas collecting vessel in fluid communication with an outlet of the sample chamber; and allowing the first gas to permeate through the solid sample from the inlet to the outlet of the sample chamber; and measuring the rate at which the pressure of the first gas rises at the outlet of the sample chamber; and using the measurements obtained to calculate permeability of the solid sample.

In an embodiment of the invention, the method further comprises measuring the diffusivity of the solid sample by: selectively placing a source of a third gas in fluid communication with the inlet side of the sample chamber so that the sample is saturated with the third gas; and selectively placing a source of the second gas in fluid communication with the outlet side of the sample chamber; and allowing the second gas to diffuse through the sample cell from the outlet side to the inlet side of the sample chamber; and measuring the second gas concentration increase over time at the inlet side of the sample chamber; and using the measurements to calculate the diffusivity of the solid sample. In preferred embodiments the source of the first gas and the source of the third gas comprise a single gas source of the same gas.

In certain embodiments of the invention, the method may be used to take measurements to calculate any of the following parameters: Viscous permeability, Knudsen flow coefficient, effective gas diffusion coefficient, tortuosity, effective porosity and effective pore length of the porous solid sample.

In certain embodiments of the invention the measurements taken for gas permeability are used to calculate any one of the following: permeability coefficient K, the viscous permeability k, and the Knudsen diffusion contribution $K_0$ by the following equation:

$$K = \frac{Q_2 p_2 L}{\Delta p A} = \frac{V\left(\frac{dp_2}{dt}\right)L}{p_1 A} = \frac{k}{\mu}p_m + \frac{4}{3}K_0\sqrt{\frac{8RT}{\pi M}}$$

where K=permeability coefficient, $Q_2$=volumetric flowrate, $p_2$=pressure at which $Q_2$ is measured, L=sample length, A=sample cross sectional area, $\Delta p$=pressure difference across the sample, k=viscous permeability, $p_m$=mean pressure, $\mu$=gas viscosity, $K_0$=Knudsen permeability coefficient, R=gas constant, T=temperature and M=molar mass of gas.

In certain embodiments of the invention, the measurements taken for gas diffusivity are used to calculate the ratio of tortuosity to effective porosity with the following equations:

$$D_{\it eff} = 10^{-6} L v C_1 / A$$

$$D_{\it eff} = E_{\it eff} D_{AB} / \tau^2$$

where $D_{\it eff}$=effective diffusion coefficient of the second gas in the third gas through the porous material, v=rate of purging of the third gas, $C_1$=second gas concentration in the third gas stream, A=sample surface area, $\epsilon_{\it eff}$=effective porosity, $\tau$=tortuosity, $D_{AB}$=free diffusion coefficient of the second gas in the third gas. When oxygen is the second gas and nitrogen is the third gas, $C_1$=oxygen concentration in nitrogen, and v=rate of nitrogen purge.

In certain embodiments of the invention, the measurements taken for gas diffusivity are used to determine either or both effective pore length and tortuosity using the following equations:

$$F = -1 + 2\sum_{n=1}^{\infty} \cos n\pi \exp\left(\frac{-D_{AB}n^2\pi^2 t}{L_{eff}^2}\right)$$

$$\frac{D_{AB}}{L_{eff}^2} = \frac{F}{t}$$

$$\tau = \frac{L_{eff}}{L}$$

where F=concentration of the second gas as a fraction of its value at infinite time, $D_{AB}$=diffusion coefficient, n=index, t=time, $L_{eff}$=effective pore length, t=time, $\tau$=tortuosity and L=sample length.

In an embodiment of the invention, the porous solid sample in the sample chamber is prepared by a method comprising: coating the whole surface of the sample core with a layer of epoxy resin and allowing the epoxy resin to set; and setting the sample core coaxially in an epoxy resin cylinder using a PTFE mould; and using a machine at either end of the sample core to expose the two faces of the sample.

BRIEF DESCRIPTION OF THE DRAWINGS

Reference is now made to the accompanying drawings, in which.

DETAILED DESCRIPTION

Figure 1:
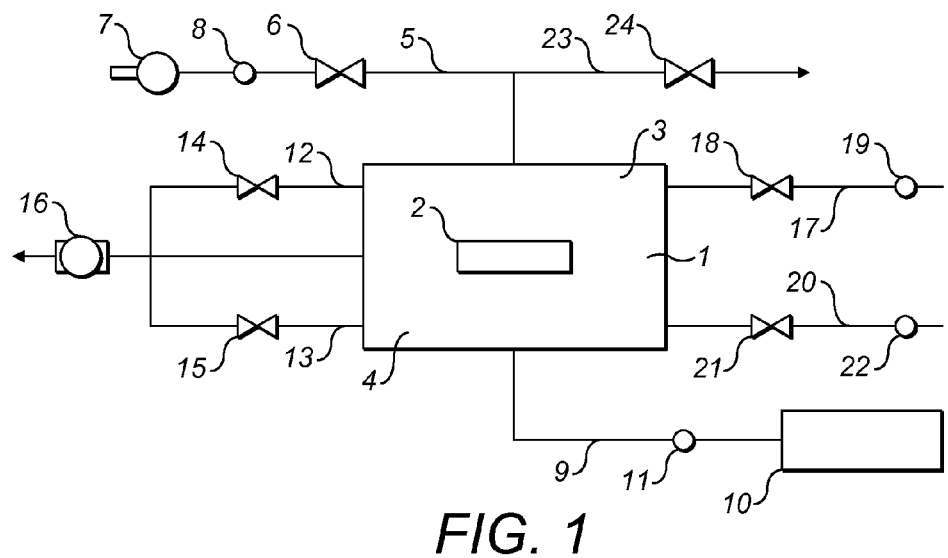
FIG. 1 is a schematic drawing of an embodiment of an apparatus, according to the invention, configured to measure permeability.

Referring to FIG. 1, the apparatus according to the invention is configured to measure permeability of the solid sample. The apparatus comprises a sample chamber 1 that includes a sample holder 2 for holding a porous solid sample for the duration of the experimental procedure. The sample chamber comprises an inlet side 3, and an outlet side 4. The apparatus comprises a first flow line 5 in fluid communication with the inlet side 3 of the sample chamber 1. The first flow line 5 has a first valve 6 disposed in it.

The first flow line 5 is in fluid communication with a first gas source 7 where the first gas is nitrogen and a first pressure measuring device, in the form of a pressure gauge 8 is disposed in the first flow line 5 between the first nitrogen source 7 and the inlet side 3 of the sample chamber 1. The first pressure measuring device is preferably a Pirani vacuum gauge.

The apparatus comprises a second flow line 9 in fluid communication with the outlet 4 of the sample chamber 1. When the apparatus is set up to measure permeability, as shown in FIG. 1, the second flow line 9 is in fluid communication with a nitrogen collecting vessel 10. A second pressure measuring device, in the form of a pressure gauge 11 is disposed in the second flow line 9 between the nitrogen collecting vessel 10 and the outlet side 4 of the sample chamber 1. The second pressure measuring device 11 is preferably a Pirani vacuum gauge or a digital manometer (Keller).

The apparatus further comprises an evacuation means for evacuating the sample chamber 1. The evacuation means comprises a third flow line 12 in fluid communication with the inlet side 3 of the sample chamber 1 and a fourth flow line 13 in fluid communication with the outlet side 4 of the sample chamber 1. A second valve 14 is disposed within the third flow line 12 and a third valve 15 is disposed in the fourth flow line 13. Both the third flow line 12 and fourth flow line 13 are in fluid communication with a vacuum pump 16.

The apparatus comprises a fifth flow line 17 in fluid communication with the inlet side 3 of the sample chamber 1. A fourth valve 18 is disposed in the fifth flow line 17. A third pressure measuring device, in the form of a pressure gauge 19 is also disposed along the length of the fifth flow line 17.

The apparatus comprises a sixth flow line 20 in fluid communication with the outlet side 4 of the sample chamber 1. A fifth valve 21 is disposed in the sixth flow line 20. A fourth pressure measuring device, in the form of a pressure gauge 22 is disposed in the sixth flow line 20.

The apparatus comprises a seventh flow line 23 with a sixth valve 24 disposed in it. The seventh flow line 23 is in fluid communication with the first flow line 5 and may be used as an exhaust to direct nitrogen gas away from the apparatus to relieve gas pressure at the inlet 3 of the sample chamber 1.

Figure 2:
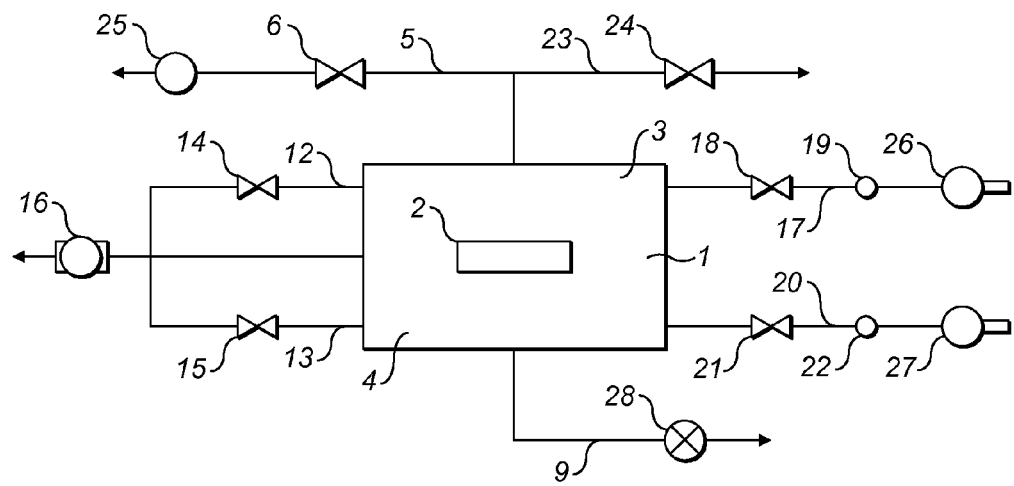
FIG. 2 is a schematic drawing of the apparatus, shown in FIG. 1, configured to measure diffusivity.

Referring now to FIG. 2, the apparatus according to the invention is configured to measure diffusivity of the solid sample. Common features of FIG. 1 and FIG. 2 are denoted by common reference numerals. The first nitrogen source 7 is has been replaced with an oxygen concentration indicator 25. The second nitrogen (where nitrogen is the third gas) source 7 is now placed in fluid communication with the fifth flow line 17 so that the third pressure measuring device 19 and fourth valve 18 are disposed between the second nitrogen source 7 and inlet side 3 of the sample chamber 1. Alternatively, a separate nitrogen source can be employed. A second gas source 27 where the second gas is oxygen is in fluid communication with the sixth flow line 20 so that the fifth valve 21 and fourth pressure measuring device 22 are disposed between the outlet side 4 of the sample chamber 1 and oxygen source 27. An oxygen flow meter 28 is placed in fluid communication with the second flow line 9.

Figure 3:
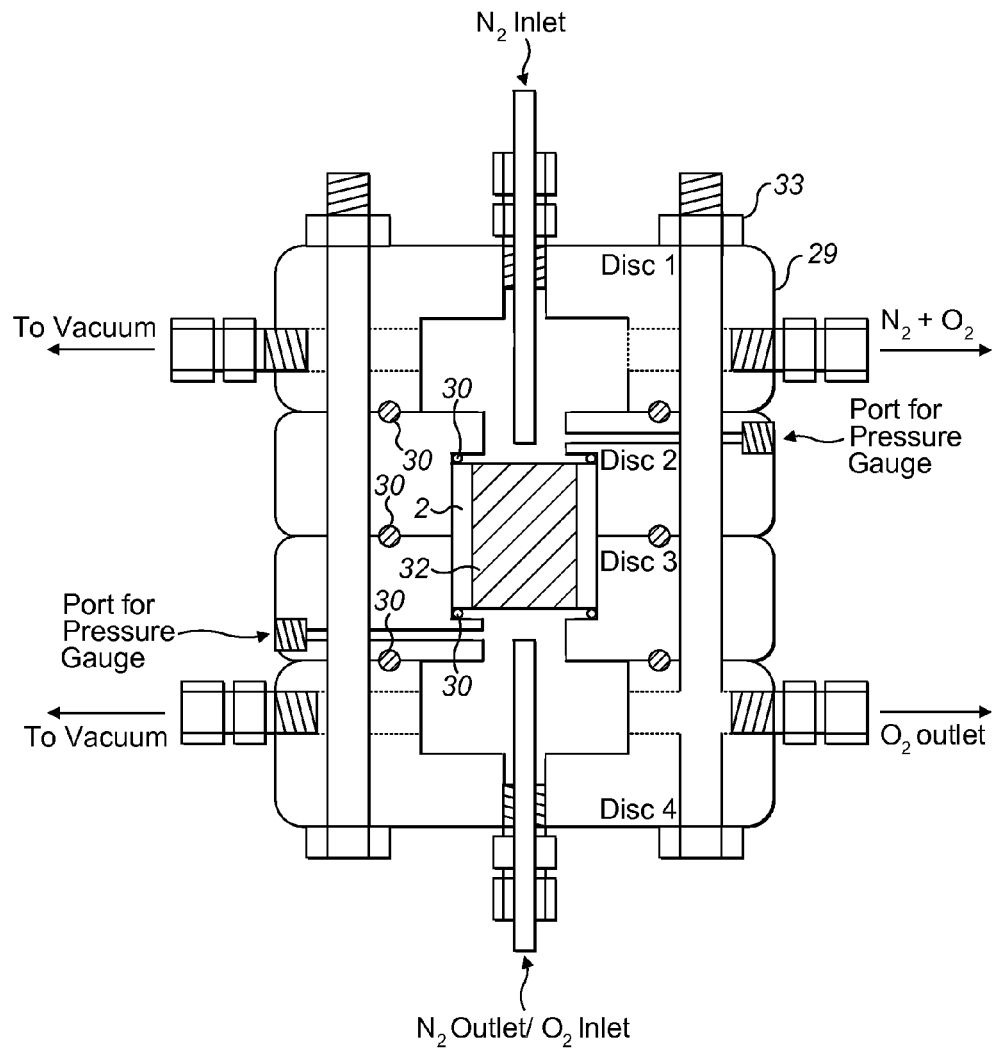
FIG. 3 is a schematic drawing of a sample chamber for use with the apparatus shown in FIG. 1 and FIG. 2.

FIG. 3 shows the sample chamber 1 in more detail. The sample chamber 1 comprises four stainless steel discs 29. The stainless steel discs 29 have O-ring seals 30 disposed between adjacent discs to ensure no gas leakage. The sample chamber 1 also comprises a sample holder 2 for containing the sample 32 for the duration of the experimental procedures, wherein O-ring seals 30 are disposed between the sample holder 2 and one or more of the four discs 29. The discs 29 each have an interengaging formation, the interengaging formations being arranged so that each disc 29 can only properly interengage a specific one of the four discs 29. In a particular embodiment, the interengaging formation comprises four tie bolts 33 and guide pins which are used to assemble the discs in the correct order before tightening of the tie bolts.

The operation of the apparatus will now be described. In the following description, the apparatus is first set up to measure the permeability of the porous solid sample, but it will be appreciated that diffusivity may be measured first instead. The sample is initially sealed in the sample holder 2 in the sample chamber 1. The apparatus is configured as in FIG. 1. The first valve 6, fourth valve 18, fifth valve 21 and sixth valve 24 are closed. The second valve 14 and third valve 15 are left open and vacuum pump 16 switched on so that the sample holder 2 containing the sample, sample chamber 1 and nitrogen collecting vessel 10 are all evacuated to a pressure of approximately 10 Pa where the pressure is monitored on the second pressure measuring device 11. The first gas (nitrogen) collecting vessel 10 preferably has a volume of approximately $2.4 \times 10^{-4}$ m$^3$ for samples with permeabilities in the range 0.1-1000 mD. A larger vessel may be used for higher permeability samples and a smaller vessel for lower permeability samples. The volume must be known for the permeability calculations. This technique is known as the pressure rise technique.

Once the sample chamber has been evacuated, the second valve 14 is opened and the outlet side 4 of the sample chamber 1 maintained at low pressure by being in fluid communication with the vacuum pump 16 and the third valve 15 left open. The first valve 6 is then opened to feed nitrogen into the inlet 3 of the sample chamber 1 and the nitrogen pressure measured by the first pressure measuring device 8. Nitrogen pressure is altered using the first valve 6 and second valve 14 simultaneously pumping nitrogen into the apparatus through the first flow line 5 and relieving nitrogen pressure via the third flow line 13 so that a constant desired nitrogen pressure reading is obtained at the inlet side 3 of the apparatus 1. Once steady conditions have been obtained, the apparatus is ready to conduct measurements for permeability. The third valve 15 is rapidly closed and nitrogen gas diffuses from the inlet side 3 of the sample chamber 1 to the outlet side 4 of the sample chamber 1 and is collected in the nitrogen collecting vessel 10. The pressure on the outlet side 4 of the sample chamber 1 is measured by the second pressure measuring device 11 and will rise at a rate dependent on the rate of entry of gas into the collecting vessel 10. The rate is recorded with the second pressure measuring device 11 and a timer.

Once the measurement is complete, the first valve 6 is closed and then third valve 15 and sixth valve 24 are opened to re-evacuate the sample chamber 1 before the next measurement is taken. The tests are repeated at various inlet pressures. Throughout the experimental procedure for measuring permeability, the fourth valve 18 and fifth valve 21 remain closed.

According to certain embodiments of the invention, the measurements taken for the permeability experiment are used to calculate the following parameters: the permeability coefficient K, the viscous permeability k and the Knudsen diffusion contribution $K_0$ with the following equation:

$$K = \frac{Q_2 p_2 L}{\Delta p A} = \frac{V\left(\frac{dp_2}{dt}\right)L}{p_1 A} = \frac{k}{\mu}p_m + \frac{4}{3}K_0\sqrt{\frac{8RT}{\pi M}}$$

where K=permeability coefficient, $Q_2$=volumetric flowrate, $p_2$=pressure at which $Q_2$ is measured, L=sample length, A=sample cross sectional area, $\Delta p$=pressure difference across the sample, k=viscous permeability, $p_m$=mean pressure, $\mu$=gas viscosity, $K_0$=Knudsen permeability coefficient, R=gas constant, T=temperature and M=molar mass of gas.

The permeability coefficient K, is calculated directly from the data of pressure change over time. There is now a linear expression for K in terms of the viscous permeability coefficient k and the Knudsen diffusion contribution $K_0$. If a linear graph is drawn between K and $p_m$, the gradient corresponds to k/$\mu$ and the y axis intercept corresponds to $$\frac{4}{3}K_0\sqrt{\frac{8RT}{\pi M}}$$

from which the $K_0$ term can be derived.

Once the measurements to calculate permeability of the solid sample have been taken, the apparatus can be easily reconfigured and set up to measure the diffusivity of the solid sample without removing the sample from the sample chamber 1. The nitrogen collecting vessel 10 and second pressure measuring device 11 are removed from the apparatus and the oxygen flow meter 28 put in their place. The first nitrogen source 7 is removed from the apparatus along with the first pressure measuring device 8, and the oxygen concentration indicator 25 put in their place. The nitrogen source 7 is placed in fluid communication with the fifth flow line 17.

The sample chamber 1 is re-evacuated by closing all valves except the second 14 and third 15 valves and switching on the vacuum pump 16. The sample is then saturated with nitrogen by opening the fourth valve 18 and monitoring the nitrogen pressure with the third pressure measuring device 19.

Steady conditions are attained when the pressure in the inlet side 3 and outlet side 4 of the sample chamber 1 are constant. Once this is achieved, oxygen is let into the outlet side 4 of the sample chamber 1 at the same pressure as the nitrogen by opening the fifth valve 21. Oxygen will then diffuse through the nitrogen filled pores of the sample and oxygen concentration in the nitrogen will gradually increase at the inlet side 3 of the sample chamber 1. This is measured by the oxygen concentration indicator 25. The oxygen concentration will eventually reach an equilibrium value.

According to certain embodiments of the invention, the measurements taken for the diffusivity experiment are used to calculate the ratio of tortuosity to effective porosity with the following equations:

$$D_{eff} = 10^{-6} L v C_1 / A$$

$$D_{eff} = \epsilon_{eff} D_{AB} / \tau^2$$

where $D_{eff}$=effective diffusion coefficient of the second gas in the third gas (oxygen in nitrogen in this embodiment) through the porous material, L=sample length, v=rate of purging of the third gas (nitrogen in this embodiment), $C_1$=concentration of the second gas in the third gas stream ($O_2$ concentration in the $N_2$ stream in this specific embodiment), A=sample surface area, $\epsilon_{eff}$=effective porosity, $\tau$=tortuosity, $D_{AB}$=free diffusion coefficient of the second gas in the third gas (oxygen in nitrogen in this embodiment).

The measurements taken for the diffusivity experiment are also used to calculate the effective pore length and tortuosity using the following equation:

$$F = -1 + 2\sum_{n=1}^{\infty} \cos n\pi \exp\left(\frac{-D_{AB}n^2\pi^2 t}{L_{eff}^2}\right)$$

$$\frac{D_{AB}}{L_{eff}^2} = \frac{F}{t}$$

$$\tau = \frac{L_{eff}}{L}$$

where F=oxygen concentration as a fraction of its value at infinite time, $D_{AB}$=diffusion coefficient, n=index, t=time, $L_{eff}$=effective sample length.

It will be appreciated that the invention described above may be modified within the spirit and scope of the following claims.

What is claimed is:

1. Apparatus for measuring the permeability and diffusivity of a porous solid comprising:
    a permeability measuring means for measuring permeability of the solid;
    a diffusivity measuring means for measuring diffusivity of the solid; and a sample chamber for holding a sample of the solid, the arrangement being such that the permeability and diffusivity can be measured without removing the sample from the sample chamber, wherein the sample chamber comprises: a plurality of discs secured together to define the sample chamber therein, wherein O-ring seals are situated between adjacent discs.

2. The apparatus according to claim 1, wherein the permeability measuring means for measuring permeability of the solid comprises a means for using a pressure rise technique.

3. The apparatus according to claim 1, wherein the sample chamber comprises:
an inlet side having an inlet;
an outlet side having an outlet;
a first flow line in fluid communication with the inlet side of the sample chamber; and
a second flow line in fluid communication with the outlet side of the sample chamber.

4. The apparatus according to claim 3, further comprising:
a first valve disposed in the first flow line.

5. The apparatus according to claim 3, further comprising an evacuation means for evacuating the sample chamber, comprising:
a third flow line in fluid communication with the inlet of the sample chamber and a vacuum pump; and
a fourth flow line in fluid communication with the outlet of the sample chamber and the vacuum pump;
whereby the vacuum pump can selectively evacuate the inlet and/or the outlet side of the sample chamber.

6. The apparatus according to claim 5, further comprising:
a second valve disposed in the third flow line;
a third valve disposed in the fourth flow line.

7. The apparatus according to claim 3, further comprising:
a source of a first gas, which can be placed selectively in fluid communication with the first flow line, whereby the first gas can be delivered to the sample chamber via the first flow line;
a first pressure measuring device for measuring pressure in the first flow line between the source of the first gas and the inlet side;
a first gas collecting vessel which can be selectively placed in fluid communication with the second flow line, whereby the first gas can be collected from the outlet side of the sample chamber after it has permeated through the solid sample core;
a second pressure measuring device for measuring pressure in the second flow line between the first gas collecting vessel and the outlet side of the sample chamber; and
a timer for measuring the rate at which pressure on the outlet side of the sample chamber rises, whereby the apparatus can be used to measure the permeability of the porous solid sample.

8. The apparatus according to claim 7, further comprising:
a fifth flow line in fluid communication with the inlet side of the sample chamber; and
a sixth flow line in fluid communication with the outlet side of the sample chamber.

9. The apparatus according to claim 8, further comprising:
a fourth valve disposed in the fifth flow line; and
a fifth valve disposed in the sixth flow line.

10. The apparatus according to claim 8, further comprising:
a flow meter which can be selectively placed in fluid communication with the second flow line instead of the first gas collecting vessel, whereby the second flow line serves as a second gas outlet line;

a source of a third gas in fluid communication with the fifth flow line, whereby the third gas can be delivered to the sample chamber via the fifth flow line to saturate the sample with the third gas;
a third pressure measuring device for measuring pressure in the fifth flow line between the source of the third gas and the inlet side;
a source of a second gas in fluid communication with the sixth flow line, whereby the second gas can be delivered to the sample chamber via the sixth flow line;
a fourth pressure measuring device for measuring pressure in the sixth flow line between the source of the second gas and the outlet side; and
a second gas concentration indicator which can be selectively placed in fluid communication with the first flow line instead of the source of the first gas, whereby the first flow line serves as a second gas and third gas outlet line, whereby the apparatus can be used to measure the diffusivity of the porous solid sample.

11. The apparatus according to claim 10, wherein the first and third gases are the same type of gas.

12. The apparatus according to claim 11, wherein the source of the first gas and the source of the third gas comprise a single gas source.

13. The apparatus according to claim 3, comprising:
a seventh flow line in fluid communication with the first flow line and an exhaust, whereby gas may flow through the seventh flow line to the exhaust, to relieve a build up of pressure in the sample chamber.

14. The apparatus according to claim 13, comprising:
a sixth valve disposed in the seventh flow line.

15. The apparatus according to claim 1, wherein the discs have an interengaging formation therein, the interengaging formation being arranged so that each disc can only properly interengage a specific one or the other discs.

16. The apparatus according to claim 15, wherein the interengaging formation comprises a plurality of tie bolts and guide pins.

17. A method of measuring the permeability and the diffusivity of a porous solid sample comprising:
evacuating a sample chamber containing the porous solid sample using a vacuum pump;
measuring the permeability of the porous solid sample and subsequently measuring the diffusivity of the porous solid sample, or vice versa;
wherein the sample chamber is configured such that the permeability and diffusivity can be measured without removing the porous solid sample from the sample chamber, and wherein the sample chamber is first evacuated by vacuum pump prior to commencing measurement of the permeability and diffusivity.

18. The method according to claim 17, wherein measuring the permeability of the sample comprises using a pressure rise technique.

19. The method according to claim 17, wherein the solid sample is sealed in a sample holder within the sample chamber prior to commencing the measurements of permeability and diffusivity.

20. The method according to claim 17, comprising measuring the permeability of the solid sample by:
selectively placing a source of a first gas in fluid communication with an inlet of the sample chamber; and
selectively placing a first gas collecting vessel in fluid communication with an outlet of the sample chamber; and
allowing the first gas to permeate through the solid sample from the inlet to the outlet of the sample chamber; and measuring the rate at which pressure of the first gas rises at the outlet of the sample chamber; and using the measurements obtained to calculate permeability of the solid sample.

21. The method according to claim 17, comprising measuring the diffusivity of the solid sample by:

selectively placing a second source of a third gas in fluid communication with the inlet side of the sample chamber so that the sample is saturated with the third gas; and selectively placing a source of a second gas in fluid communication with the outlet side of the sample chamber; and allowing the second gas to diffuse through the sample cell from the outlet side to the inlet side of the sample chamber; and measuring the second gas concentration increase over time at the inlet side of the sample chamber; and using the measurements to calculate the diffusivity of the solid sample.

22. The method according to claim 21, wherein the first and third gases are the same type of gas.

23. The method according to claim 22, wherein the source of the first gas and the source of the third gas comprise a single gas source.

24. The method according to claim 17, whereby the method is used to take measurements to calculate any of the following parameters:

Viscous permeability, Knudsen flow coefficient, effective gas diffusion coefficient, tortuosity, effective porosity and effective pore length of the porous solid sample.

25. The method according to claim 17, whereby the measurements taken for gas permeability are used to calculate any one of the following:

permeability coefficient K, the viscous permeability k, and the Knudsen diffusion contribution $K_0$ by the following equation:

$$K = \frac{Q_2 p_2 L}{\Delta p A} = \frac{V\left(\frac{dp_2}{dt}\right)L}{p_1 A} = \frac{k}{\mu}p_m + \frac{4}{3}K_0\sqrt{\frac{8RT}{\pi M}}$$

where K=permeability coefficient, $Q_2$=volumetric flowrate, $p_2$=pressure at which $Q_2$ is measured, L=sample length, A=sample cross sectional area, $\Delta p$=pressure difference across the sample, k=viscous permeability, $p_m$=mean pressure, $\mu$=gas viscosity, $K_0$=Knudsen permeability coefficient, R=gas constant, T=temperature and M=molar mass of gas.

26. The method according to claim 17, whereby the measurements taken for gas diffusivity are used to calculate the ratio of tortuosity to effective porosity with the following equations:

$$D_{eff}=10^{-6}LvC_1/A$$

$$D_{eff}=E_{eff}D_{AB}/\tau^2$$

where $D_{eff}$=effective diffusion coefficient of the second gas in the third gas through the porous material, v=rate of purging of the third gas, $C_1$=second gas concentration in the third gas stream, A=sample surface area, $\epsilon_{eff}$=effective porosity, $\tau$=tortuosity, $D_{AB}$=free diffusion coefficient of the second gas in the third gas.

27. The method according to claim 17, whereby the measurements taken for gas diffusivity are used to determine either or both of effective pore length and tortuosity using the following equations:

$$F = -1 + 2\sum_{n=1}^{\infty} \cos n\pi \exp\left(\frac{-D_{AB}n^2\pi^2 t}{L_{eff}^2}\right)$$

$$\frac{D_{AB}}{L_{eff}^2} = \frac{F}{t}$$

$$\tau = \frac{L_{eff}}{L}$$

where F=second gas concentration as a fraction of its value at infinite time, $D_{AB}$=diffusion coefficient, n=index, t=time, $L_{eff}$=effective pore length, t=time, $\tau$=tortuosity and L=sample length.

28. The method according to claim 17, whereby the porous solid sample in the sample chamber is prepared by a method comprising:

coating the whole surface of the sample core with a layer of epoxy resin and allowing the epoxy resin to set; and setting the sample core coaxially in an epoxy resin cylinder using a polytetrafluoroethylene (PTFE) mold; and using a machine at either end of the sample core to expose the two faces of the sample.

29. The method according to claim 17, wherein evacuating the sample chamber comprises evacuating the sample chamber to a pressure of about 10 Pa or less.

* * * * *

UNITED STATES PATENT AND TRADEMARK OFFICE
CERTIFICATE OF CORRECTION

PATENT NO. : 8,447,537 B2
APPLICATION NO. : 12/711697
DATED : May 21, 2013
INVENTOR(S) : Alexander Bismarck et al.

It is certified that error appears in the above-identified patent and that said Letters Patent is hereby corrected as shown below:

In the Specifications:

Column 5, line 2, replace "$F = -1 + 2\sum_{n=1}^{\infty} \cos n\pi \exp\left(\frac{-D_{AB}n^2\pi^2 t}{L_{eff}^2}\right)$" with -- $F = -1 + 2\sum_{n=1}^{\infty} \cos n\pi \exp\left(\frac{-D_{AB}n^2\pi^2 t}{L_{eff}^2}\right)$ --

Column 5, line 5, replace "$\frac{D_{AB}}{L_{eff}^2} = \frac{F}{t}$" with -- $\frac{D_{AB}}{L_{eff}^2} = \frac{F}{t}$ --

Column 8, line 45, replace "$F = -1 + 2\sum_{n=1}^{\infty} \cos n\pi \exp\left(\frac{-D_{AB}n^2\pi^2 t}{L_{eff}^2}\right)$" with -- $F\ -1 + 2\sum_{n=1}^{\infty} \cos n\pi \exp\left(\frac{-D_{AB}n^2\pi^2 t}{L_{eff}^2}\right)$ --

Column 8, line 49, replace "$\frac{D_{AB}}{L_{eff}^2} = \frac{F}{t}$" with -- $\frac{D_{AB}}{L_{eff}^2} = \frac{F}{t}$ --

In the Claims:

Column 12, line 22, replace "$F = -1 + 2\sum_{n=1}^{\infty} \cos n\pi \exp\left(\frac{-D_{AB}n^2\pi^2 t}{L_{eff}^2}\right)$" with -- $F = -1 + 2\sum_{n=1}^{\infty} \cos n\pi \exp\left(\frac{-D_{AB}n^2\pi^2 t}{L_{eff}^2}\right)$ --

Column 12, line 24, replace "$\frac{D_{AB}}{L_{eff}^2} = \frac{F}{t}$" with -- $\frac{D_{AB}}{L_{eff}^2} = \frac{F}{t}$ --

Signed and Sealed this
Twenty-third Day of July, 2013

Teresa Stanek Rea
*Acting Director of the United States Patent and Trademark Office*